United States Patent [19]

Ballermann et al.

[11] Patent Number: 5,843,781
[45] Date of Patent: Dec. 1, 1998

[54] IMPLANTABLE PROSTHETIC VASCULAR DEVICE HAVING AN ADHERENT CELL MONOLAYER PRODUCED UNDER SHEAR STRESS

[75] Inventors: Barbara J. Ballermann, Cockeysville; Mark J. Ott, Baltimore, both of Md.

[73] Assignee: The Johns Hopkins University School of Medicine, Baltimore, Md.

[21] Appl. No.: 583,490

[22] Filed: Jan. 4, 1996

Related U.S. Application Data

[63] Continuation of Ser. No. 54,794, Apr. 28, 1993, abandoned.
[51] Int. Cl.[6] .............................. C12N 5/00; C12N 11/08; A61F 2/00
[52] U.S. Cl. ........................ 435/400; 424/424; 424/93.3; 424/93.7; 435/180; 435/363; 435/366; 435/373; 435/395; 435/396; 435/402
[58] Field of Search ..................... 435/240.242, 240.243, 435/395, 396, 400, 402, 180, 363, 364, 373; 424/422, 424, 93.3, 93.7

[56] References Cited

U.S. PATENT DOCUMENTS

| | | | |
|---|---|---|---|
| 3,883,393 | 5/1975 | Knazek et al. | 435/240.242 |
| 4,804,628 | 2/1989 | Cracauer et al. | 435/240.242 |
| 5,015,585 | 5/1991 | Robinson | 435/240.242 |
| 5,037,378 | 8/1991 | Muller et al. | 435/240.242 X |
| 5,162,225 | 11/1992 | Sager et al. | 435/240.243 |

OTHER PUBLICATIONS

Olesen, et. al., Nature, vol. 331, Jan. 1988 (pp. 168–170).
Aohn, et. al., Int. J. Microcirc: Clin. Exp, 9, 411–422, 1990.

*Primary Examiner*—David M. Naff
*Attorney, Agent, or Firm*—Fish & Richardson, P.C.

[57] ABSTRACT

A device having a surface coated with a firmly adherent cell monolayer is produced by culturing adherent cells in the presence of the surface in vitro under conditions of continuous shear stress of from 0.4 dyne/cm$^2$ to 33 dyne/cm$^2$ produced by the force of circulating fluid medium in contact with the cells. The surface may be contained by an implantable device, or a culture or fermentation vessel. Preferably, an endothelial cell monolayer is produced on a surface of a prosthetic vascular device made of polypropylene. In a hollow fiber cartridge device, endothelial cells are grown under shear stress on the inner surface of the lumen of a hollow fiber and perivascular cells are grown on the outer surface of the fiber. Growing cells under continual stress more closely approximates the in vivo environment where blood passes over the endothelium in a blood vessel, and produces a cell monolayer closely resembling naturally occurring firmly adherent cell layers found in vivo in the lining of blood vessels. The endothelial cells may be transfected with a gene and the surface of the device may be pre-coated with extracellular matrix protein.

11 Claims, 11 Drawing Sheets

IMPLANTABLE PROSTHETIC VASCULAR DEVICE HAVING AN ADHERENT CELL MONOLAYER PRODUCED UNDER SHEAR STRESS

This is a continuation of application Ser. No. 08/054,794, filed Apr. 28, 1993, now abandoned.

BACKGROUND OF THE INVENTION

1. Field of the Invention

The present invention relates generally to culture of cells in vitro and specifically to an in vitro method of producing a device coated with endothelial cells under conditions of continuous shear stress.

2. Description of the Related Art

Culture of endothelial cells in vitro is most commonly performed under static conditions such as in a culture dish or flask with stationary medium. However, since endothelial cells form the inner lining of blood vessels, they are normally exposed to continuously flowing blood as opposed to static conditions. This creates varying degrees of chronic shear stress that acts on the endothelial cells. Even during blood vessel development (angiogenesis), endothelial cells are continuously exposed to flow, and are never in a static environment. It is therefore desirable to study the biology of endothelial cells and prepare the cells for use in vivo under conditions closely resembling those in vivo, specifically under chronic shear stress.

Shear stress is the frictional force produced by fluid as it moves past a solid. Shear stress is dependent on the configuration of the fluid path, the viscosity of the fluid and the rate of fluid flow. For cylindrical tubes containing flowing Newtonian fluid, shear stress is calculated as follows:

$$\tau = \frac{4nQ}{\pi r^3}$$

where n=dynamic viscosity, Q=flow rate and r=inner radius of the cylinder In vitro systems previously described for the study of shear stress on endothelial cells fall into three groups, namely cone-plate rheometers, parallel plate perfusion systems and glass capillary perfusion systems. The cone-plate rheometer consists of a flat plate over which is suspended a rotating cone (Dewey, et al., *J.Biomech.Engr.*, 103:177, 1981; Davies, et al., *Proc.Natl.Acad.Sci. USA*, 83:2114, 1986; Ando, et al., *Biorheology*, 27:675, 1990). The angle between plate and cone, the rate of rotation of the cone and the viscosity of the fluid between plate and cone determine the shear stress to which cells growing on the plate are exposed. Advantages of this system are that the shear stress can be accurately determined, that shear stress can be varied instantaneously and can be varied without concomittant changes in hydraulic pressure, and, with modification, the system allows direct observation of the cells under shear stress.

The parallel plate perfusion system consists of two glass plates brought in close apposition, with one of the plates containing the cells (Wechezak, et al., *J.Cellular Physiol.* 139:136, 1989; Gupte et al, In Vitro *Cell. Dev. Biol.* 26:57, 1990; Ando, et al., In Vitro *Cell. Dev. Biol.* 24:871, 1988; Frangos, et al., *Biotechnol. Bioengineering* 32:1053, 1988). Fluid flows between the two plates over the surface of the endothelial cells. To enhance cell adhesion, the glass is pretreated with NaOH, which confers a negative charge to the glass. The advantages of the system are that it allows ready access to the cells for microscopic observation, and that it is technically much simpler and therefore less expensive than the cone-plate apparatus.

The glass capillary perfusion system consists of glass capillary tubes into which the endothelial cells are seeded, and through which medium flows (Olesen, et al., *Nature*, 331:168, 1988; Hohn, et al., *Int.J.Microcirc:Clin.Exp.*, 9:411, 1990). Given the cylindrical nature of the capillary, shear stress tends to be rather uniform in the capillary, except at entry and exit points, an assumption that cannot be as easily made for the parallel plate apparatus. The principal advantage of this system lies in its simplicity, and presumably, the low cost. In addition, cells located at the exit point of the capillary are accessible for patchclamp work.

One problem found in prior art systems described include growth of only a limited number of cells (e.g. $10^5$ cells) at any given time under any given condition. Therefore, studies in which significant quantities of RNA or cell culture supernatants must be harvested cannot be done. Large quantities of RNA are required to establish cDNA libraries, to perform Northern blotting analyses and to perform RNAse protection assays. Also, large quantities of cell supernatants are required to characterize and purify materials secreted by the cells under flow.

Most of the current systems allow study under shear stress for only a brief period of time (minutes to hours). Therefore, a system which would allow the cells to be grown under flow for several days would be a desirable advance. Typically, existing systems require that cells be established first under static conditions, and then switched to flow conditions. In addition, the switch from static conditions to flow conditions is a very unphysiologic stimulus since endothelial cells do not exist under static conditions in vivo. Therefore a system in which cells could be grown under flow from the time of seeding would be much closer to the in vivo situation.

The study of chronic cell-cell interactions in vitro necessitates co-culture of distinct cell types in such a way that the cells are kept separate but are able to interact. The present systems cannot accomplish co-culture in this manner. The importance of co-culture lies in the fact that a large number of cell-cell interactions occur in the perivascular space in vivo and these interactions are likely to be influenced by endothelial cell shear stress.

All of the existing systems described above utilize culture material such as glass or plastic which are not similar to that used for vascular grafts in humans. Thus, existing systems for the study of endothelial cell shear stress do not mimic the behavior of endothelial cells on clinically useful prosthetic vascular materials. A desirable system would allow the study of the effects of shear stress on endothelial cell adhesion to prosthetic surfaces pertinent to clinical use.

Artificial vascular grafts suffer the shortcoming that the materials tend to be thrombogenic, thus limiting their use to larger vessels. Production of grafts of small caliber made non-thrombogenic by an established monolayer would be a great advance in vascular surgery. However, endothelial cell adhesion is usually poor when the cells are pre-seeded onto artificial material under static conditions.

The ease with which endothelial cells of animal origin will replicate on artificial prostheses in vitro mimics the in vivo environment in which growth on vascular grafts from anastomotic sites is only a few centimeters. The ability of endothelial cells to replicate in culture and form confluent monolayers in vitro on implantable biomaterials would allow the development of techniques useful for the treatment of a variety of diseases.

The present invention addresses the needs of the scientific and medical community by providing a method for producing a device coated with highly adherent cells wherein the cells more accurately reflect the growth pattern observed in vivo.

SUMMARY OF THE INVENTION

The present invention arose from the discovery of a method for producing a device coated with a firmly adherent cell monolayer. The inventors have determined that the culture of endothelial cells under continuous shear stress accurately mimics the in vivo environment of the cells, in contrast to previous methods utilizing static culture conditions. A device produced by the method of the invention is useful for vascular grafts, including artificial heart valves, vascular access grafts for dialysis or other forms of hemoperfusion and potentially any implantable device containing artifical blood vessels or capillaries, in which non-endothelial cells are co-cultured with endothelial cells.

DETAILED DESCRIPTION OF THE INVENTION

The present invention provides a method for producing a device having a surface coated with a firmly adherent cell monolayer. The method comprises culturing the adherent cells in the presence of the surface of the device under conditions of continuous shear stress to produce the monolayer on the surface. The device produced by such a method is useful as an implantable structure in vivo.

Certain basic problems in growing cells to densities and/or to structures approaching those of living tissues include problems with a means of supplying nutrient medium to the cells. The present invention provides a method of culturing cells which overcomes many of the basic problems associated with producing an artificial organ-like device in vitro which can be utilized in vivo.

Producing an artificial organ-like device in vitro which contains an adherent cell monolayer or a surface of the device faces various problems. One problem is that components of the medium must diffuse through the cell layers to reach all cells; this diffusion becomes more difficult as the thickness of the cell layer increases.

Another problem associated with growing an artificial organ-like device in vitro is the maintenance of a suitable microenvironment in conventional cell culture. Thus, the fluid immediately adjacent to the growing cell is continuously changing as cellular metabolism proceeds and is returned to its original status only in stepwise fashion when the culture medium is changed or agitated.

A third problem is the requirement of a suitable material for a lattice or suitable material upon which to grow the monolayer. In the present invention, cells suspended in a nutrient medium are initially allowed to settle on the surface of the device, such as capillaries or fibers, through which oxygenated nutrient medium continuously flows. Nutrient substances pass from the perfusing medium through the capillary wall and into the cell, while cell products e.g., lactic acid and hormones pass from the cell through the capillary wall and into the perfusate. These products may be recovered by suitable means.

The method of the present invention overcomes these problems and in one embodiment provides for growth of cells under conditions of continuous shear stress, wherein the device contains at least one cell culture unit, along with a medium reservoir, a gas exchanger, and a pump to provide controlled flow rates of the perfusate. By producing the adherent cell monolayer under continuous shear stress, the monolayer closely resembles naturally occurring firmly adherent cell layers found in vivo, such as the lining of blood vessels.

The device to be coated with an adherent cell monolayer can be any structure which is useful for implanting in a subject or for studies of interaction between cells and soluble factors produced by those cells. For example, the device may be an implantable biomaterial which is used as a prosthetic vascular device. Artificial vascular grafts tend to be thrombogenic thereby limiting their use to larger vessels. Production of non-thrombogenic grafts of small dimensions can be accomplished by the method of the invention. Examples of such vascular grafts include coronary artery bypass grafts, peripheral vascular bypass grafts, prosthetic heart valves and vascular access grafts for any type of hemoperfusion such as dialysis or plasmaphoresis. Alternatively, the method of the invention can be used to produce an adherent cell monolayer as a surface of a culture or fermentation vessel, such as a hollow fiber culture device or cartridge.

The cells used in the method of the invention are seeded directly onto a surface of the device under flow, or "continuous shear stress" in vitro. "Continuous shear stress" refers to the force of the medium on the cells that occurs due to continual circulation of the medium. The amount of shear stress will vary with the size, shape and contour of the device used for culture. The appropriate shear stress is dependent on the configuration of the fluid path, the viscosity of the fluid and the rate of fluid flow. These parameters can be easily determined by one of skill in the art without resorting to undue experimentation. By growing the cells under continual stress, the device more closely approximates the in vivo environment, for example, where blood passes over the endothelium in a blood vessel.

Cells grown according to the method of the invention should possess the property of being able to form a monolayer on a surface substrate of the device. Initial attachment of cells may be accomplished by any means which allows the cell to grow as a monolayer on a device. Attachment enhancing surfaces can be produced directly, such as by selecting appropriate plastic polymers for the device or, indirectly, as by treating the surface in the device by a secondary chemical treatment. Therefore, "attachment" refers to the ability of a cell to adhere to a surface in a culture device, wherein the attachment promoting surface is in direct contact with the cells, which otherwise would grow in a three-dimensional cellular aggregate in suspension. Attachment, or adherence, of a cells to the device surface allows them to produce a monolayer. In the absense of shear stress, endothelial cell adhesion remains weak. Techniques for modifying surfaces for enhancing adherence of cells are well known in the art.

Preferably the cells grown by the method of the invention are grown under levels of shear from about 0.4 dyne/cm$^2$ to about 33 dyne/cm$^2$ and most preferably from about 1dyne/cm$^2$ to about 14 dyne/cm$^2$. At these levels, the cells do not dislodge and remain sufficiently attached to the surface of the device to form an adherent monolayer.

In addition to interactions with soluble factors, most cells in vivo are in contact with an extracellular matrix, which is a complex arrangement of interactive protein and polysaccharide molecules which are secreted locally and assemble into an intricate network in the spaces between cells. According to the method of the invention, the addition of an extracellular matrix protein to the surface of the culture device forms an insoluble matrix which allows cells in culture to adhere in a manner which closely corresponds to the in vivo extracellular matrix. The adherent cell-coated device of the invention can be preferably produced by coating the surface of a device, such as a hollow cartridge, with a polybasic amino acid composition to allow initial attachment of the cell. Such compositions are well known in the art and include polyornithine and polylysine. Alternatively, the surface of the device may be coated with a known extracellular matrix or matrix-like protein composition to enhance the cell's ability to grow and form a monolayer on the substrate. Such compositions include laminin, collagen, fibronectin and Pronectin F. Other extracellular matrix proteins that can be used will be apparent to one of skill in the art.

In a preferred embodiment of the invention, the material on which the cells are grown is similar to that used for vascular or other grafts. Preferably, the method of the invention uses a device which is composed of polypropylene material. Alternatively, prosthetic devices composed of materials such as dacron or expanded polytetrafluoroethylene can be used. Other materials which allow endothelial cell adhesion to the surface when the cells are grown under shear stress in vitro from the moment of seeding will be known to those of skill in the art.

Preferred adherent cells grown according to the method of the invention are endothelial cells. Examples of endothelial cells include vascular, retinal capillary, glomerular, corneal, aortic and brain capillary cells. The cells may be derived from many species including bovine, rat, human, rabbit and porcine. Preferably, the cells utilized in the implant are species specific, therefore, endothelial cells from a human would be used for an implant intended for a human subject, for example.

At the time of seeding, the cultures can be analyzed for endothelial cell-specific function to ensure the homogeneity of the cell population. Functional assays which are specific for endothelial cells include uptake of acetylated low density lipoprotein (LDL) and the presence of von Willebrand's factor. Additionally, assays for the presence of antigens specific for smooth muscle cells, such as alpha and gamma-actin isoforms, can be used to rule out potential contamination with smooth muscle cells.

The method of the invention allows cells to be co-cultured in combination with other cell types in the device. "Co-culture" refers to the growth of more than one type of cell in a shared environment so that the cells are physically separated, but still able can interact such that growth factors and other secreted soluble mediators produced by a cell can interact with another cell. This type of co-culture is similar to the in vivo environment where cell-cell interactions occur in the perivascular space, for example. Typically, these interactions are influenced by endothelial cell shear stress and, as a result, the method of the invention closely resembles the in vivo situation.

The method of the invention for culturing cells typically entails co-culture of two types of cells, preferably endothelial cells and perivascular cells. Preferred perivascular cells are vascular smooth muscle cells, mesangial cells, pericytes, fibroblasts or epithelial cells for example.

The cells may be grown using a hollow cartridge device which contains at least one fiber for growth of the cells. The lumen inside the fibers is referred to as the inner lumen and the lumen outside the fibers is referred to as the outer lumen. Preferably, endothelial cells are grown in the inner lumen and perivascular cells are grown on the outer lumen. Media flows continuously through the inner lumen thus creating a constant shear force which is physiologically similar to the in vivo environment of vascular tissue.

The cells grown by the method of the invention can be transfected with a gene. A major complication of current interventions for vascular disease, such as balloon angioplasty or endarterectomy, is disruption of the artherosclerotic plaque and thrombus formation at sites of local tissue trauma. Genetically altered endothelial cells could minimize local thrombosis. In addition, such altered cells grown using the method of the invention may be useful for the treatment of myocardial or tissue ischemia by introducing cells expressing thrombolytic, angiogenic, or growth factor genes into the graft. Because of its contiguity with the bloodstream, the endothelium is an attractive target for the delivery of functional genes in vivo. The use of endothelium for gene transfer would permit secretion of a recombinant protein from genetically engineered endothelial cells directly into the blood. Alternatively, endothelial cells expressing a nonsecreted recombinant protein might be able to inactivate a toxic substance that is circulating in the blood.

For transfection of a eukaryotic cell, such as an endothelial cell, standard methods of transfection of DNA including calcium phosphate co-precipitates, conventional mechanical procedures such as microinjection, insertion of a plasmid encased in liposomes, or virus vectors may be used. Eukaryotic cells can also be cotransformed with DNA sequences encoding a gene product of interest, and a second foreign DNA molecule encoding a selectable phenotype, such as the herpes simplex thymidine kinase gene (*Current Protocols in Molecular Biology,* Wiley Interscience). Another method is to use a eukaryotic viral vector, such as simian virus 40 (SV40) or bovine papilloma virus, to transiently infect or transform eukaryotic cells and express the protein. (*Eukaryotic Viral Vectors,* Cold Spring Harbor Laboratory, Gluzman ed., 1982).

Isolation and purification of expressed polypeptides, or fragments thereof, produced in vitro by the cells grown according to the method of the invention, may be carried out by conventional means including preparative chromatography and immunological separations involving monoclonal or polyclonal antibodies. Such techniques are standard and common in the art.

Genes which may be transfected into cells forming the monolayer include genes which encode proteins which promote angiogenisis, reduce thrombosis, promote repopulation, inhibit neo intimal smooth muscle cell hyperplasia, mediate vasodilation or other therapeutic proteins. For example, endothelial cells could be transfected with t-PA (Friezner, et al., *J. Biol. Chem.* 261:6972, 1986) or $PLA_2$ (Sharp, et al., *J. Biol. Chem.*, 266:14850, 1991) to inhibit thrombogenicity. Another example includes the incorporation of the vascular endothelial growth factor gene to selectively promote angiogenesis in the absence of smooth muscle proliferation (Fischer, et al,, *J. Biol. Chem.*, 266:11947, 1991).

The following examples are intended to illustrate, but not limit the invention. While they are typical of those that might be used, other procedures known to those skilled in the art may alternatively be utilized.

EXAMPLE 1

Production of an Adherent Cell Monolayer on a Cell Culture Cartridge

Figure 1A:
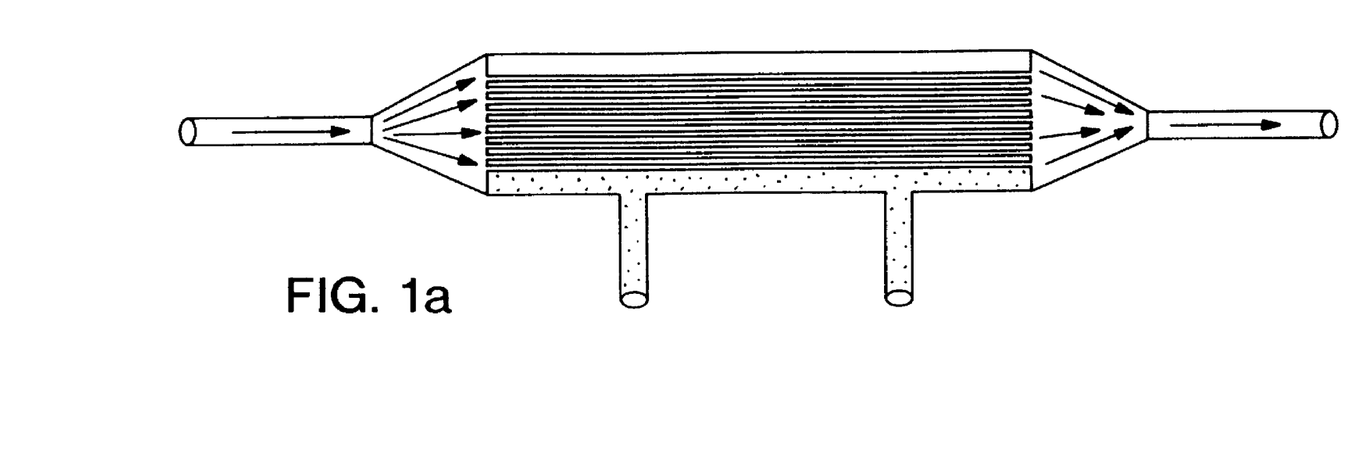
FIGS. 1a–c show schematically the configuration of the cell culture cartridge, and the location of growing cells in a cross-section of a fiber.
Figure 1B:
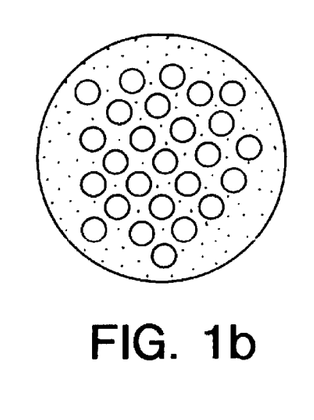
Figure 1C:
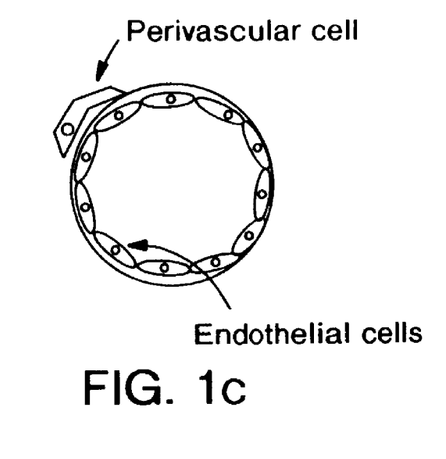

The 4 station pump (Cellmax Quad), gas permeable tubing and polypropylene cartridges were from Cellco, Inc. (Germantown, Md.). ProNectin F solution was from Protein Polymer Technologies, Inc. (San Diego, Calif.). Injection sites were from Quest Medical, Inc. (Dallas, Tex.). Cell culture media and serum were from Gibco BRL (Gaithersburg, Md.). Glomerular endothelial cells were derived from bovin calf kidneys according to methods described previously (Ballermann, B. *Am.J.Physio.* 256:C182, 1989). The configuration of the cell culture cartridge is shown in FIG. 1, and the location of the growing cells is shown schematically in a cross-section of a fiber.

The male Luer lock caps were removed and the sterile cartridge was drained of PBS. Each port was then capped with an injection site (Quest Medical, Inc., Dallas, Tex.). Once capped all of the following procedures were performed with syringes and 20 gauge needles. Before each injection, the injection site to be entered was cleaned with an alcohol swab.

With the long axis of the cartridge in the vertical position, 5 ml of a 1:20 ProNectin F solution (Protein Polymer Technologies, Inc., San Diego, Calif.) was injected into the bottom port to completely fill the inner lumen of the cartridge. The ProNectin F solution was left in the cartridge at room temperature for 2 hours. Every 15 minutes, the cartridge was shaken and rotated to a different resting plane. After 2 hours, the inner lumen was drained of the ProNectin F.

The cartridge was washed thoroughly with PBS as the ProNectin F diluant is extremely toxic to cells. The inner lumen was washed with 30 cc of sterile PBS followed by washing of the outer lumen also with 30 cc of sterile PBS. This washing procedure was repeated three times and then both lumens were drained of PBS. The inner and outer lumens were filled with media containing 1% fetal bovine serum.

Endothelial cells were trypsinized from cell culture plates and suspended in 5 ml of RPMI with 1% FBS to achieve a cell concentration of $0.5–1.0 \times 10^7$ cells/ml, and injected into the cartridge. The cartridge was turned so that the long axis was horizontal with the side injection ports vertical and placed in the incubator at 37° C. in an atmosphere of 5% $CO_2$ in air for 45 minutes. A second cell suspension of similar concentration was then prepared and injected into the cartridge. The cartridge long axis was again placed horizontal and the cartridge rotated 90 degrees so that the side injection ports were horizontal. The cartridge was placed into the incubator for 45 minutes. This process was repeated two more times, each time rotating the cartridge 90 degrees, so that the inner lumen of the cartridge was turned a full 360 degrees about its long axis. After the last 45 minute incubation, the cartridge was gently flushed with 15 cc of RPMI with 15% FBS and FGF (4 ng/ml) and the outer lumen was flushed with 30 cc of the same.

The reservoir tubing and ball value apparatus were filled with medium by removing the male Luer lock caps from the sterile tubing and joining both ends with a double male Luer lock adaptor (Cobe, Lakewood, Colo.). The reservoir was filled with 70 mls of medium and was hand pumped through the system until the entire circuit was filled with medium. Approximately 20 cc was required to fill the tubing. The tubing was then clamped on either side to prevent any flow.

The tubing on the now seeded cartridge was also clamped on each long axis end. With the cartridge long axis horizontal, the injection site was removed from the end of the cartridge. The pump tubing containing the double male Luer lock adaptor was unscrewed so that the adaptor remained on the thicker tubing which comes directly from the pump and is the inflow tubing. This was then hooked onto the open cartridge inflow port. (It is important to keep the amount of air in the inflow system to a minimum).

A second double male Luer lock adaptor was hooked to the open pump outflow tubing. The injection port was removed from the other end of the cartridge and that was joined to the open end of the double male Luer lock adaptor (this then became the outflow port). Invariably there will be some air in the system on the outflow side, but it will be removed when the medium circulates through the reservoir. It is important to avoid air bubbles from passing through the cartridge as they will strip cells off the fibers. Air bubbles can also collect on the inflow port and produce an airlock on some of the upper fibers thereby preventing equal flow to all the fibers.

The clamped tubing was unclamped and the cartridge and tubing was hand pumped a few times to assure proper flow. The system was then connected to the mechanical pump. Flow was started at the lowest setting for several days to allow the cells the best opportunity to attach. The medium was changed every two days. To vary the viscosity, dextran (70–2000) was added to the culture medium at a concentration of 5–10%. The medium was then sterile filtered. The viscosity was measured with a Cannon-Manning semi-micro capillary tube viscometer (International Research Glassware, Kenilworth, N.J.).

EXAMPLE 2

Giomerular Cell Culture

For the culture of glomerular endothelial cells under flow, hollow fiber cartridges containing bundles of 175 or 230 polypropylene fibers each 13 cm in length and 330 $\mu$m in diameter were used. The cartridges are similar in design to hemodialysis cartridges, namely medium can be circulated independently through the inner lumen and around the external surface of the hollow fibers. A medium reservoir was connected to the hollow fiber cartridge via gas permeable tubing. The tubing contains a compressible chamber with two unidirectional valves at the entry and exit ports (pumping chamber). The pump system contains 4 pump heads, which operate by cyclical compression of the pumping chamber, thus producing unidirectional flow (FIG. 1).

The pump system and the flow paths with the hollow fiber cartridges all sit in a water-jacketed cell culture incubator in humidified atmosphere of 5% $CO_2$ in air. The pump rate is adjusted with a control unit which sits outside the incubator. In addition, the pump heads are exchangeable such that the degree of compression of the pump chamber can be controlled independently. Control of the pump speed and pump head size allow variations in the rates of fluid flow ranging from 2.5 to 50 ml/min. This translates to a calculated shear stress in each fiber of ~1 to 20 dyne/cm², assuming a medium viscosity the same as water. For these experiments the medium viscosity is adjusted under dextrans. The range of shear stress achieved in the presence of 5% dextran-70 is ~3–60 dyne/cm². In each experiment (and for each change in pump speed/pump head size), medium flow rates are measured independently by determining the fluid volume exiting each cartridge as a function of time. The CellMax Quad system was adapted by the PI for endothelial cell culture during the past 2 years. This system was not previously used for culture of cells in the lumen of the fibers under flow.

Fluid viscosity is determined independently using a Cannon-Manning semi-micro capillary tube viscometer (International Research Glassware, Kenilworth, N.J.) which is suspended in a water bath at 37° C. For the purpose of these studies, it is assumed that the level of shear stress does not significantly alter fluid viscosity.

Glomeruli were isolated under sterile conditions from bovine calf kidneys obtained from a local slaughterhouse (Rupersberger's, Baltimore) as previously published (Ballermann, B., Am. J. Physiol, 256:C182, 1989). The purity of the preparation was checked by microscopy; glomerular preparations less than 95% pure are discarded. The glomeruli were subjected to collagenase (CLS III, Worthington) digestion for 45 minutes at 37° C. Glomerular remnants were removed by centrifugation for 5 minutes at 100×g. The remaining cell suspension was sedimented at 800×g (5 minutes), and plated at cloning density on gelatin-coated plates in RPMI 1640 medium containing 15% fetal bovine serum, 8 ng/ml acidic FGF (R&D Systems Inc., Minneapolis) and 0.1 μg/ml heparin (Sigma) and incubated in a humidified atmosphere of 5% $CO_2$ in air. Cloning density refers to the dilution of cells at which 5–15 single colonies form per 100 cm². To achieve this, serial dilutions of the primary cell suspension ranging from 1:10–1:10,000 are plated. Typically, cells plated at 1:100 to 1:1000 are at cloning density. The medium was changed every 48 hours and when endothelial cell colonies appeared (usually 10–14 days after plating), they were selected with cloning cylinders, detached with trypsin/EDTA and passed to new plates again at cloning density. Usually new endothelial cell clones appeared within 10 days. These were again selected with cloning cylinders, detached with trypsin/EDTA and individual colonies passed to wells of 12-well plates. Once cloned, the primary endothelial cells were expanded. For expansion, the endothelial cells were passed just prior to reaching confluence at a 1:3 split. Once the cells were no longer at cloning density the concentration of α-FGF was reduced to 4 mg/ml. All of the cultures were performed on gelatin-coated plates. The cells were cloned twice because after the first round of cloning many of the cultures still contained a few mesangial cells, which overgrew the culture within a few weeks if not removed. The identity of the endothelial cells was always verified using acetylated LDL uptake. To visualize acetylated LDL uptake, endothelial cells were grown on glass coverslips, washed with medium containing 2% serum, and then incubated with 10 mg/ml fluoresent acetylated LDL (Biomedical Technologies, Stoughton, Mass.) for 3 hours. Cells were then washed with PBS and observed by fluorescence microscopy.

The inner lumen of the polypropylene fibers was first coated with 0.05 mg/ml Pronectin F (Protein Polymer Technologies, Inc.) in PBS for 2 hours, followed by extensive washing of the inner and outer aspects of the fibers with PBS. Cells harvested with trypsin/EDTA from static culture plates were then introduced at a concentration of ~$5\times10^6$ cells/ml in RPMI 1640 medium containing 1% PBS to fill the lumen of the fibers (~5 ml). Pronectin F is a synthetic protein polymer containing multiple repeats of the RGD fibronectin binding site. During attachment the serum concentration in the medium was kept low to prevent competitive interaction of cell integrins with soluble fibronectin in serum. After 45 minutes of incubation at 37° C. in a humidified atmosphere of 5% $CO_2$ in air with the cartridge in the horizontal plane, unattached cells are gently flushed out, and the seeding protocol is repeated an additional 3 times, each time the cartridge is rotated 90° to assure circumferential cells attachment. At the end of the fourth attachment period, the medium was replaced with RPMI 1640 containing 15% serum and 4 ng/ml α-FGF with 0.1 μg/mi heparin and the cartridges were connected to flow at venous (1–1.5 dyne/cm²) levels. The medium was changed every 48 hours.

Glomerular endothelial cells were seeded into Pronectin-F coated polypropylene fibers, and maintained in culture for 9 days. In some of the cartridges medium was continually circulated around the extraluminal surface of the fibers (0 shear stress). Some of the cartridges were kept at venous levels of shear for nine days (~1.5 dyne/cm²) (Low Flow Chronic, LFC). In some of the cartridges, venous levels of shear were used initially, and then arterial levels of shear (13–15 dyne/cm²) were imposed for the last 1 (High Flow Acute, HFA) or 5 (High Flow Chronic, HFC) days of the nine day period. Cells grown on Pronectin F coated plastic cover slips in cell culture plates served as additional "static" controls. Cells were then fixed and processed for transmission and scanning electron microscopy.

Adhesion

Cells grown in cartridges with 0 Shear stress initially attached. However, after 9 days in culture, acute shear stress at a level of ~10 dyne/cm² to cells accustomed to a no stress environment; removed most of the cells from the cartridge. By contrast, the same level of shear stress did not dislodge the cells that had been grown under flow. Table 1 shows one experiment each for bovine glomerular (GEN) and bovine aortic (BAE) endothelial cells. The cells grown chronically under shear stress adhered more firmly to the fibers than cells not previously accustomed to shear.

TABLE 1

NUMBER OF CELLS DISLODGED AFTER ADAPTATION
TO VARIOUS SHEAR STRESS CONDITIONS

| CHRONIC SHEAR LEVEL | GEN-1[a] | GEN-2[b] | BAE (± SE)[c] |
|---|---|---|---|
| 0 | $2390 \times 10^4$ | $480 \times 10^4$ | $1223 \pm 273 \times 10^4$ |
| LFC | $708 \times 10^4$ | $43 \times 10^4$ | $113 \pm 51 \times 10^4$ |
| HFC | $87 \times 10^4$ | $11 \times 10^4$ | $11 \pm 7 \times 10^4$ |
| HFA | $45 \times 10^4$ | $4 \times 10^4$ | $6 \pm 3 \times 10^4$ |

[a,b]Results of two separate experiments.
[c]Results of five separate experiments.

The precise total cell number contained in each cartridge could not be determined, since the cells in the cartridges accustomed to chronic flow could not be removed even with prolonged trypsin treatment. One possible explanation for the finding in Table 1 is that there were substantially fewer cells contained in the cartridges accustomed to flow. However, since scanning electron microscopy consistently showed confluent monolayers of cells in those cartridges, whereas few adherent cells were seen in the cartridge in the cartridges prepared under 0 shear stress conditions, the data were interpreted to indicate that chronic culture of endothelial cells under shear stress markedly stimulated cell adhesion to the underlying material.

Figure 2:
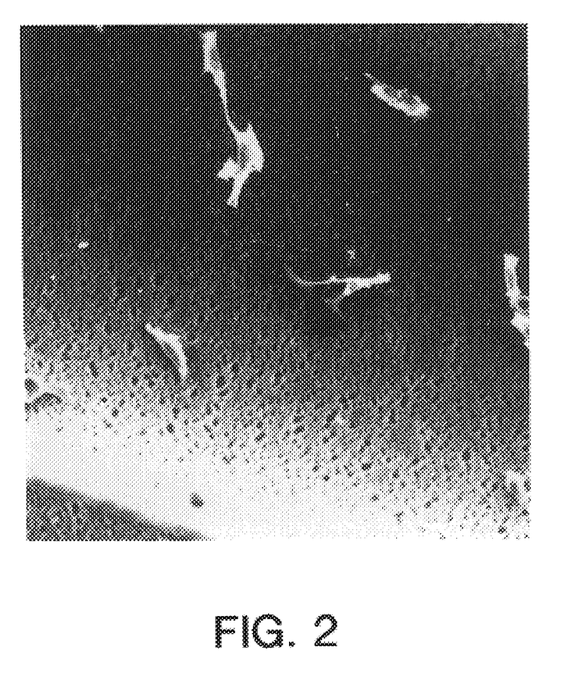
FIG. 2 shows endothelial cells grown under 0 shear stress.
Figure 3:
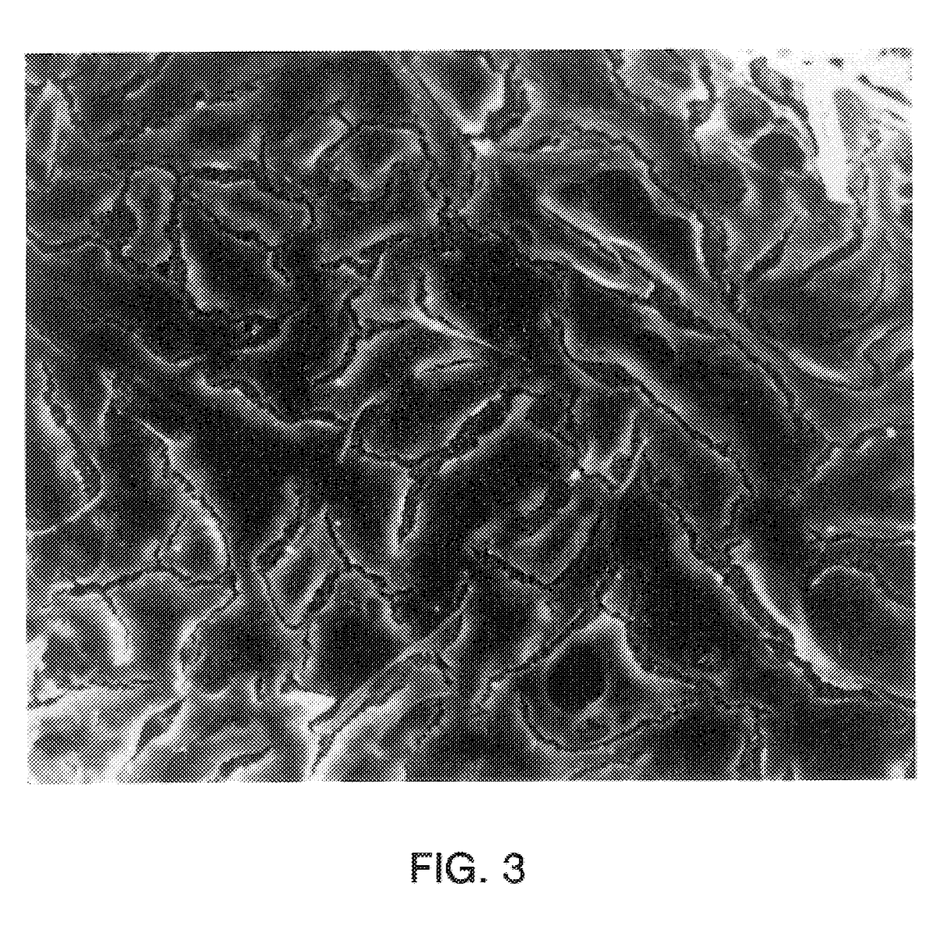
FIG. 3 shows cells grown at high flow acute (HFA) (13–15 dyne/cm$^2$ for the last day of nine days of culture).

Scanning electron microscopy for cartridges with glomerular endothelial cells grown under 0 shear is shown in FIG. 2, for cells grown at HFA in FIG. 3. After adaptation to 0 shear conditions for 9 days, few cells remain sufficiently attached to withstand an ~10 dyne/cm² flush (see also Table 1).

After adaptation to shear at 1.5 dyne/cm² followed by 15 dyne/cm², cells do not detach from the fibers with a ~10 dyne/cm² flush. The large "craters" observed in some of the cells were only observed under arterial, not under venous levels of flow. As judged by transmission EM, these may represent areas of highly attenuated cytoplasm. It is not yet known whether this phenomenon also occurs in endothelial cells from large vessels.

RNA Isolation

Cells under varying shear stress/hydraulic pressure conditions were taken from the incubator and the cartridge was flushed with 30 cc of DEPC treated ice-cold PBS. The PBS was drained and immediately replaced with ice-cold 4.0 guanidine isothiocyanate (GTC) followed by shaking for 45 minutes (at 4° C.). The GTC solution was then collected from the cartridge by pushing it back and forth in the fibers several times with syringes. The resulting material was then homogenized and total RNA recovered by ultracentrifugation on a cesium-TFA gradient. The usual yield for one confluent cartridge was ~300 µg total RNA. Poly (A)+RNA was then purified from total RNA using oligo(dT)-cellulose.

$^3$[H]Thymidine Incorporation

Cartridges were flushed with Hanks' balanced salt solution. The cartridges were then incubated for 3 hours with medium containing 2% serum and 1 µCi/ml $^3$[H]Thymidine. The thymidine was removed, the fibers flushed/incubated 3×30 minutes with 6% ice-cold TCA, washed once with acetic methanol at −20° C., and dried. Individual fibers (equal lengths) were then cut from the cartridge, the cells in each fiber were solubilized and incorporation of radioactivity for individual fibers was determined.

EXAMPLE 3

Morphological Studies

Scanning and transmission EM studies were performed with cells grown for 9 days under various flow conditions. Morphological studies indicated a significant flattening of the cells grown under flow (FIG. 4) and the expression of dense arrays of actin filaments and dense bodies at the base of the cells (FIG. 5a) compared to a poorly developed array of actin filaments in cells grown on coverslips under static conditions (FIG. 5b). In many areas cells grown under shear stress became extremely flattened with fenestrae formation (FIG. 5c). To date, Weibel Palade bodies have not been seen on transmission EM of cells grown in static culture; they were easily found in cells grown under shear stress (FIG. 5d). Finally, with regard to cell adhesion and confluence of the monolayers, FIG. 5e shows a fiber end on, with the monolayer shrunken away from the polypropylene. The basolateral surface of the cells contains numerous projections, which are seen to "burrow" into the polypropylene fiber by transmission EM (FIG. 5a). In FIG. 5e, the fact that the monolayer is nearly complete is also well demonstrated.

Figure 4:
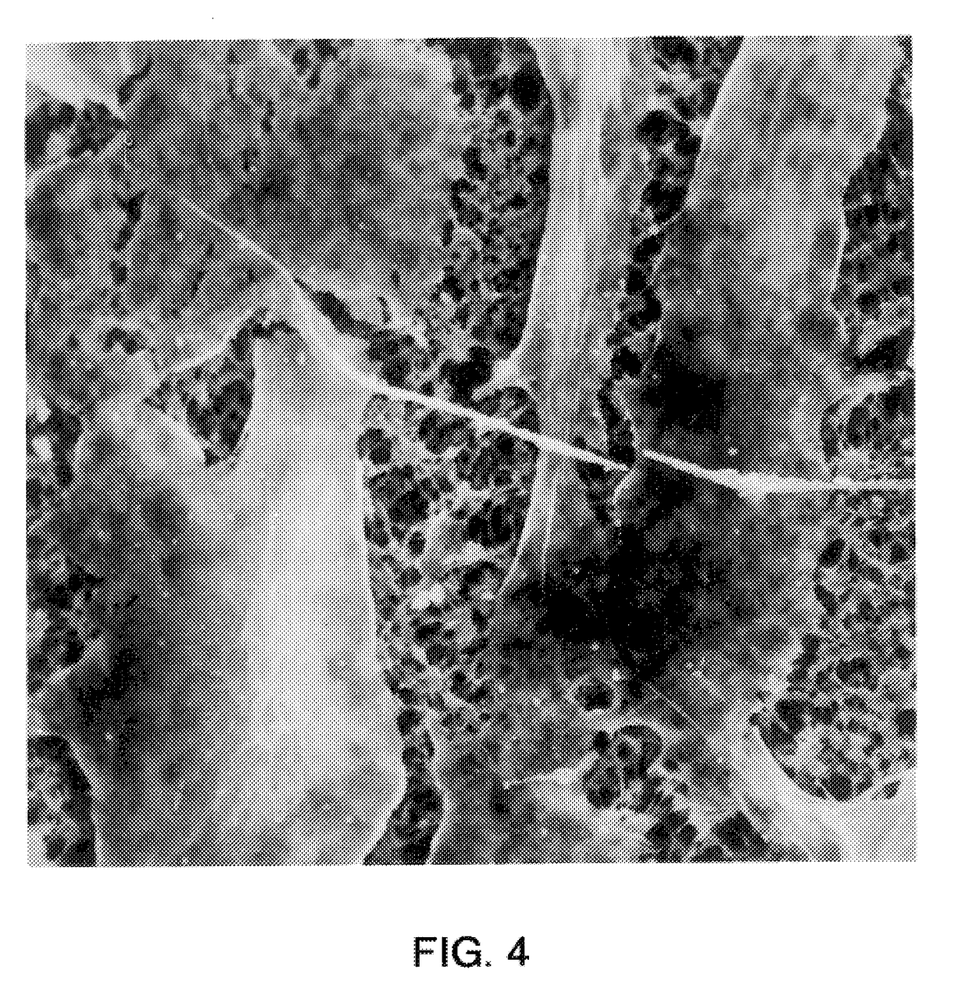
FIG. 4 shows scanning and transmission electron microscopy (EM) studies of cells grown under flow.
Figure 5A:
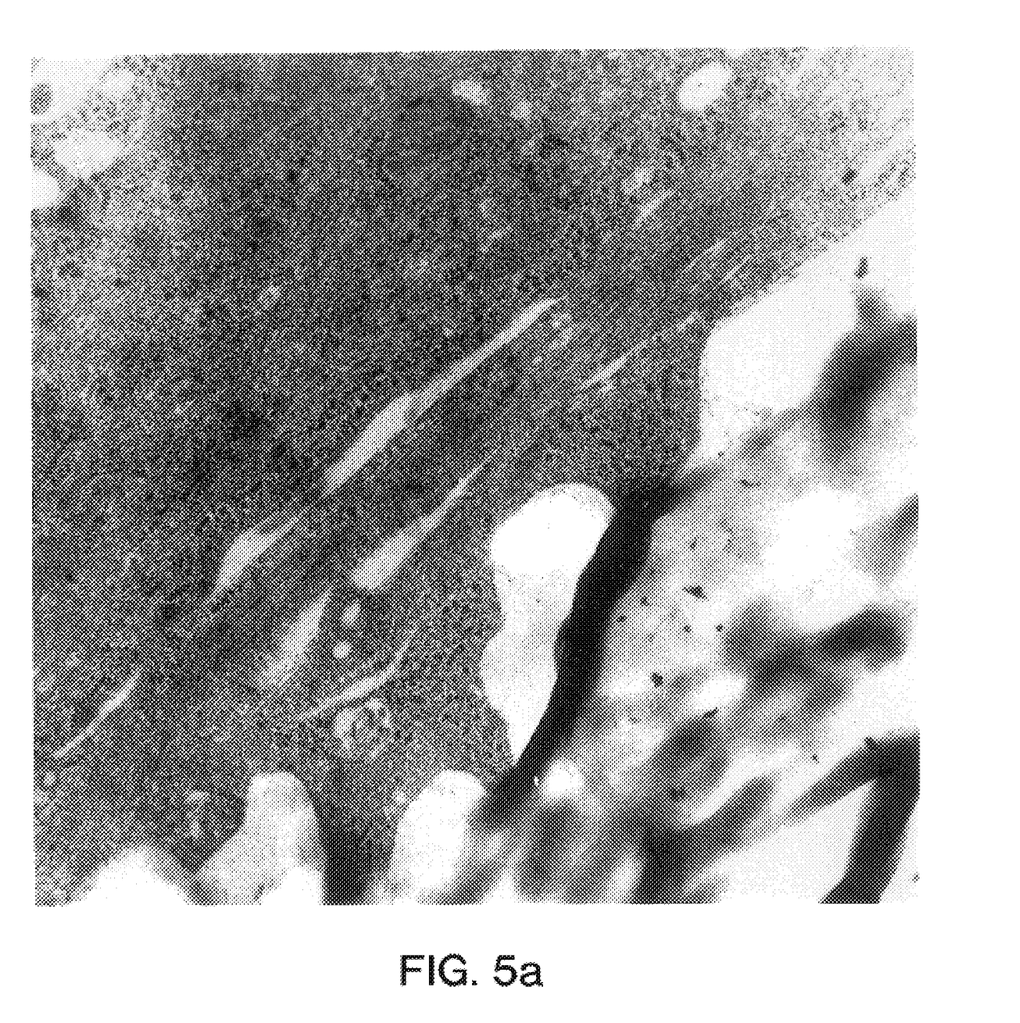
FIG. 5a shows the expression of actin in cells grown under flow.
Figure 5B:
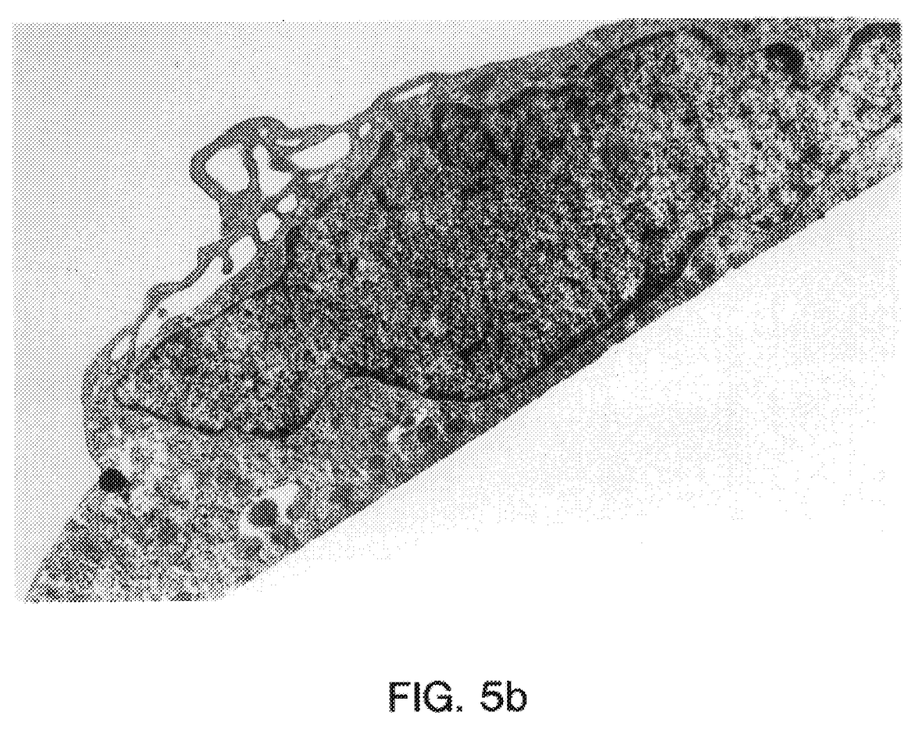
FIG. 5b shows scanning and transmission EM scanning and transmission EM of cells grown under static conditions.
Figure 5C:
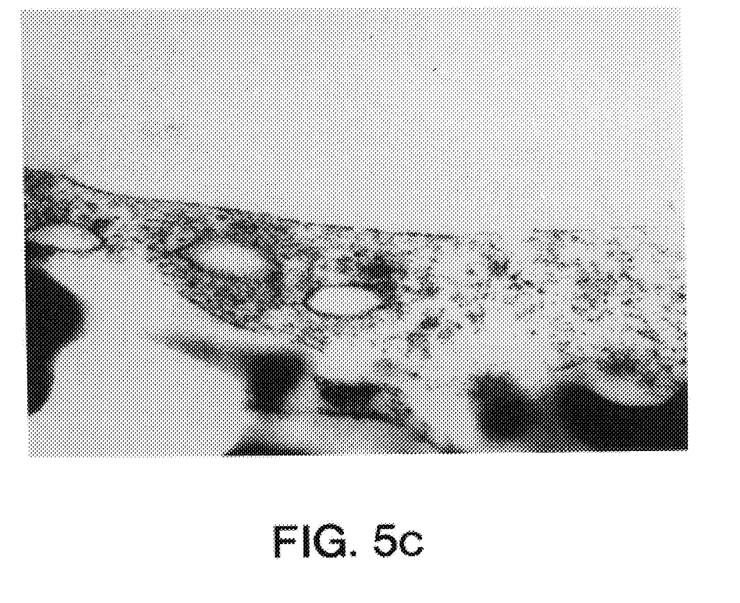
FIG. 5c shows scanning and transmission EM of cells grown under shear stress flattened with fenestral formation.
Figure 5D:
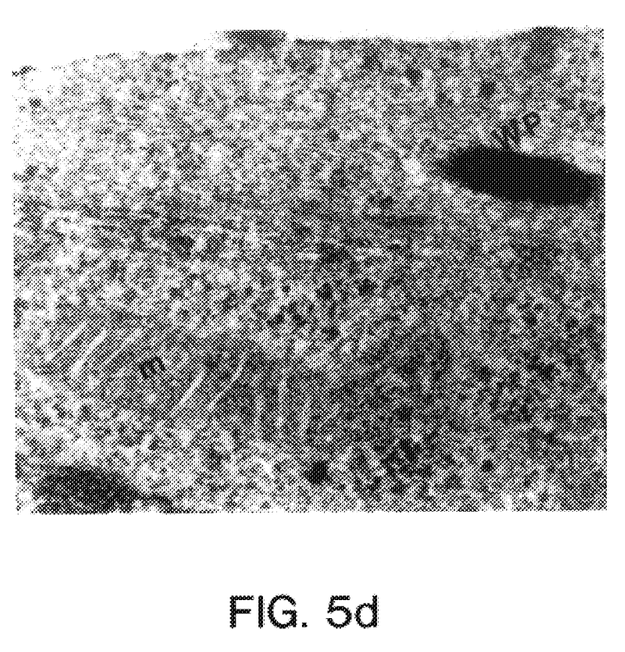
FIG. 5d shows scanning and transmission EM of Weibel Palade bodies of cells grown under shear stress.
Figure 5E:
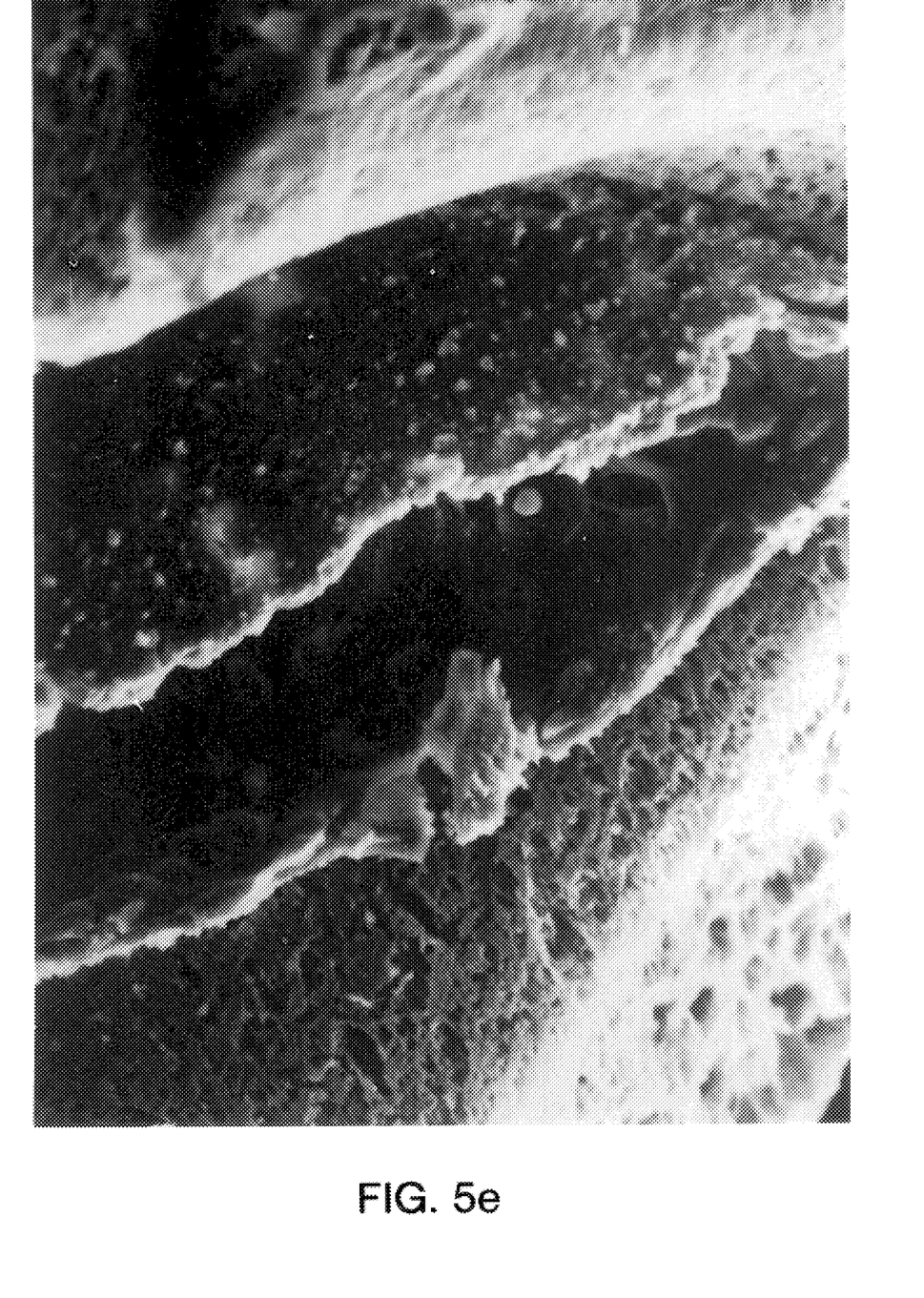
FIG. 5e shows scanning and transmission EM of a polypropylene fiber containing glomeruler endothelial cells adapted to shear for 9 days.

FIG. 4 shows that after adaptation to shear at 1.5 dyne/cm² for 7 days, glomerular endothelial cells take on an extremely flattened appearance. FIG. 5a shows transmission EM of glomerular endothelial cells grown under flow (venous level shear stress, 9 days). Cells grown at any level of flow consistently showed a highly organized and dense array of actin filaments with dense bodies. The cells also contain a large number of ribosomes, suggesting a high rate of protein synthesis. Furthermore, the cells seemed to send anchoring projections into the underlying polypropylene fibers.

FIG. 5b shows glomerular endothelial cells grown on a cover slip under static conditions (compare with FIG. 5a). The cells contained few actin filaments and the density of ribosomes was less than that in cells grown under flow.

FIG. 5c is an example of an extremely attenuated area of cytoplasm with 3 fenestrae. Whether the degree of fenestral development is a function of time and level of shear stress or merely represents a phenotypic change of endothelial cells grown on permeable supports is unknown. FIG. 5d shows an example of a Weibel Palade Body (large arrow). A mitochondrion in the same field (small arrow) is shown for comparison.

FIG. 5e shows a polypropylene fiber containing glomerular endothelial cells adapted to shear for 9 days seen end on. The cells have lifted off the fiber during fixation. The basolateral cell surface (left lower corner) contains numerous anchoring projections. A circumferential monolayer is seen.

EXAMPLE 4

Mitogen Synthesis

The effect of shear stress on the synthesis and secretion of mitogenic factors was studied. Given previous studies suggesting that glomerular hemodynamics may be casually related to glomerular sclerosis (Brenner, B., Am. J. Physiol. 249:F324, 1985), conditioned medium (no serum) from glomerular endothelial cells adapted to 0, venous or arterial levels of shear was examined for mitogenic activity on glomerular epithelial and mesangial cells. The cell to medium ratio was adjusted by dilution prior to determination of mitogenic activity.

Figure 6:
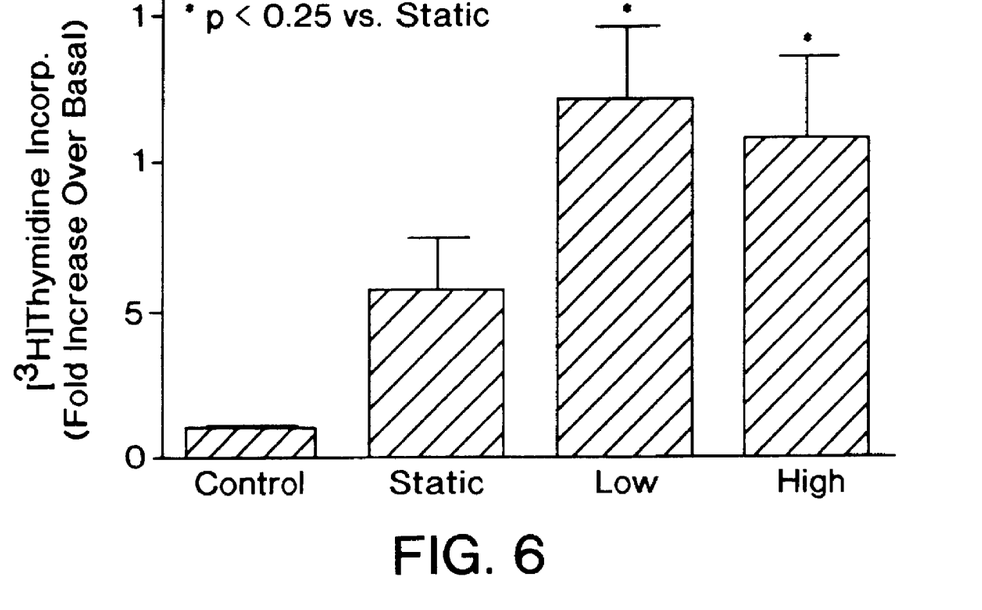
FIG. 6 shows the mitogenic effect of endothelial cell conditioned medium on quiescent glomerular epithelial cells.

Control medium was not previously exposed to endothelial cells. There was a significant increase in mitogenic activity in medium harvested from glomerular endothelial cells under shear stress, though the level of shear stress did not significantly alter mitogen release. The findings for mesangial cell mitogenic activity were similar. FIG. 6 shows the mitogenic effect of endothelial cell conditioned medium on quiescent glomerular epithelial cells.

Figure 7:
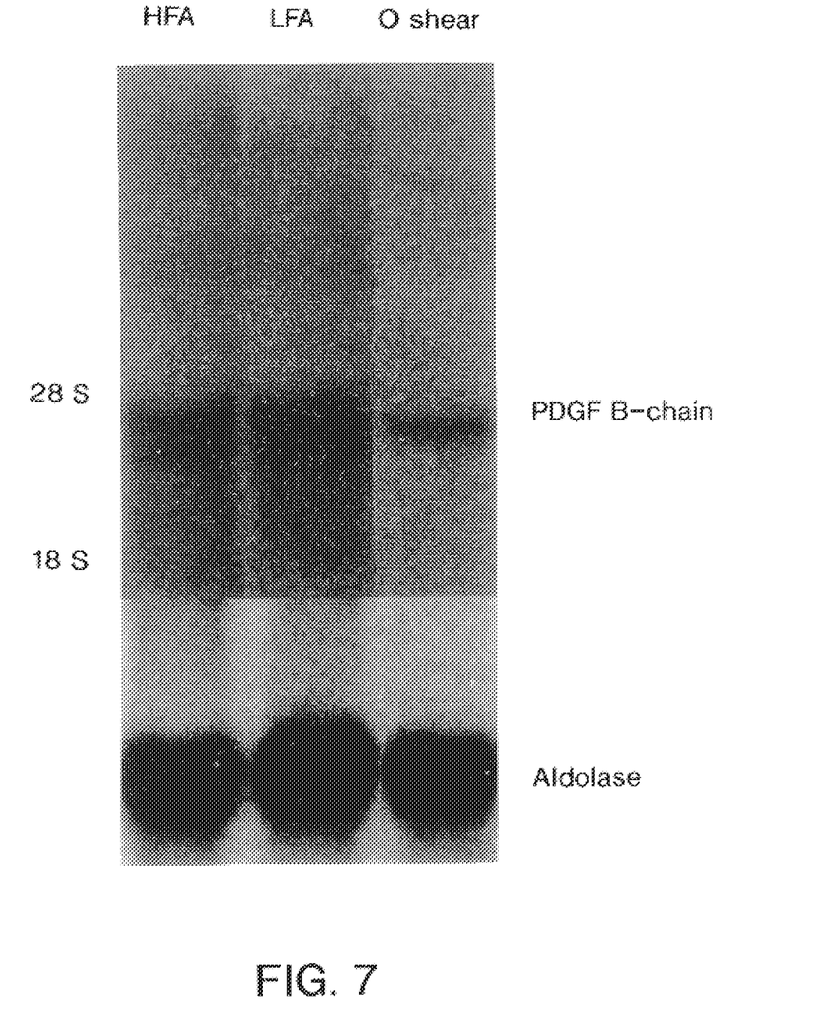
FIG. 7 shows a Northern blot analysis of total RNA from endothelial cells under flow and probed with PDGF-A and PDGF-B chain cDNAs.

FIG. 7 shows total RNA was harvested from the endothelial cells under flow and subjected to Northern blot analysis with PDGF-A and PDGF-B chain cDNAs; hybridization with a cDNA for aldolase served to demonstrate equivalent loading. As can be seen, culture of glomerular endothelial cells under shear stress HFA and LFC markedly stimulated PDGF-B chain mRNA expression, though the level of shear stress did not have an independent effect. PDGF-A chain mRNA was much less abundant, and was not increased in cells exposed to shear stress. Therefore mitogenic activity in supernatants from glomerular endothelial cells grown under shear stress may be due to expression of PDGF.

EXAMPLE 5

Studies on Vasoactive Mediators

Figure 8:
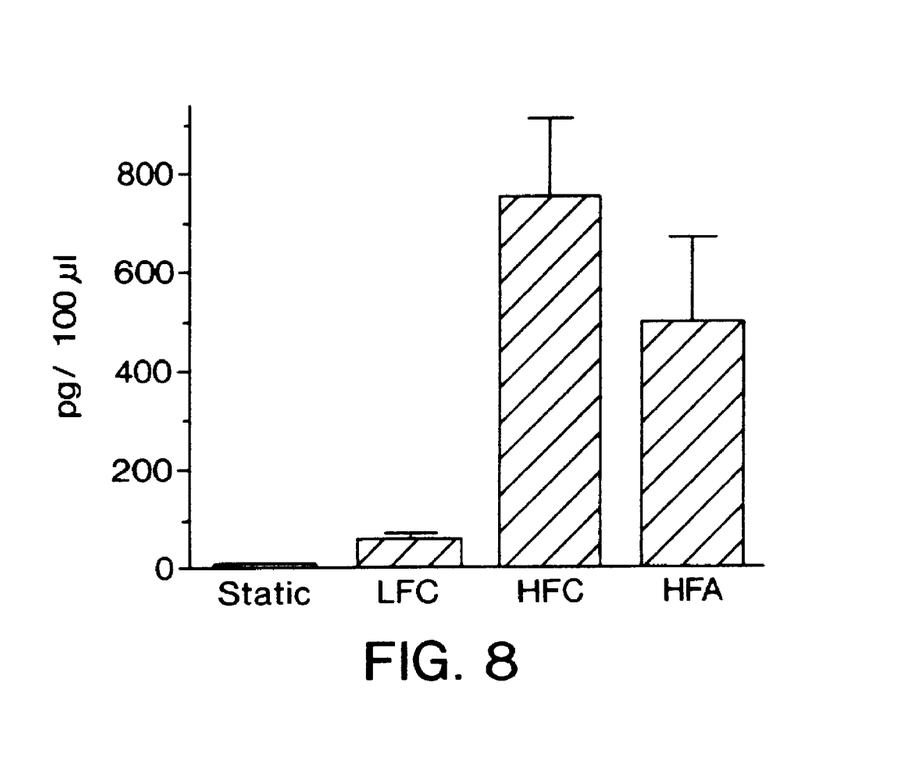
FIG. 8 shows a radioassay of PGF$_{1\alpha}$ accumulation in cells grown under static, LFC, HFA and HFC conditions.

Vasoactive mediator release by glomerular endothelial cells under shear stress was also studied. Cells were grown under static, LFC, HFA and HFC conditions in 10% serum for 9 days. Accumulation of 6-keto $PGF_{,,}$ (prostacyclin metabolite) and endothelial-1 in the medium during the last 24 hours of culture was then determined by radioimmunoassay. Data points represent values for 3 separate experiments and were corrected for the medium volume:cell number ratio. FIG. 8 shows 6-keto $PGF_{1\alpha}$ accumulation as a function of shear stress.

All levels of shear stress significantly augmented 6-keto $PGF_{1\alpha}$ accumulation by comparison with static conditions. Furthermore, cells grown at arterial levels of flow either for 24 hours or 5 days released approximately 10 fold more 6-keto $PGF_{1\alpha}$ than cells grown at venous levels of shear. Thus, there was a chronic induction of prostacylin release with arterial levels of shear stress, possibly reflecting continued activation of cell membrane signalling events, or possibly induction of the $PLA_2$ enzyme by high shear.

Medium from the same cartridges as those used for experiments in FIG. 8 was also assayed for endothelin-1 accumulation.

Table 2 shows endothelin-1 accumulation (fmol/100 μl) over 24 hours as a function of shear stress levels in three experiments.

TABLE 2

| EXPT. | 0 SH. | LFC | HFA | HFC |
|---|---|---|---|---|
| 1 | 544 | 1670 | 3970 | 1792 |
| 2 | 635 | 2372 | 1420 | 2740 |
| 3 | 552 | 12387 | 2820 | 7605 |

0 SH = No Shear Force.

Endothelin-1 accumulation was much more variable than 6-keto $PGF_{1\alpha}$ accumulation (FIG. 8). Medium from cells exposed to shear consistently contained more endothelin-1 than medium from static cells, though the level of shear stress had no apparent effect.

The foregoing is meant to illustrate, but not to limit, the scope of the invention. Indeed, those of ordinary skill in the art can readily envision and produce further embodiments, based on the teachings herein, without undue experimentation.

We claim:

1. A method for producing an implantable prosthetic vascular device comprising providing a hollow fiber cartridge device containing at least one hollow fiber having an inner lumen surface inside the fiber and an outer lumen surface outside the fiber, seeding endothelial cells on the inner lumen surface and perivascular cells on the outer lumen surface, culturing the endothelial cells under a continuous shear stress of from 0.4 dyne/$cm^2$ to 33 dyne/$cm^2$ to produce an adherent endothelial cell monolayer on the inner lumen surface and culturing the perivascular cells to produce a layer of perivascular cells on the outer lumen surface.

2. The method of claim 1, wherein the perivascular cells are selected from the group consisting of vascular smooth muscle cells, mesangial cells, pericytes, fibroblasts and epithelial cells.

3. The method of claim 1, wherein the hollow fiber is made of polypropylene material.

4. The method of claim 1, wherein the endothelial cells are stably transfected with at least one gene.

5. The method of claim 4, wherein the gene encodes a protein which reduces thrombogenicity.

6. The method of claim 5, wherein the gene is selected from the group consisting of t-PA and $PLA_2$.

7. The method of claim 4, wherein the gene encodes a vasodilating mediator.

8. The method of claim 4, wherein the gene encodes an angiogenic factor.

9. The method of claim 1, wherein the inner lumen surface is pre-coated with an extracellular matrix protein.

10. The method of claim 9, wherein the extracellular matrix protein is selected from the group consisting of fibronectin, laminin, and collagen.

11. An implantable prosthetic vascular device produced by the method of claim 1.

* * * * *